(12) United States Patent
Holmes et al.

(10) Patent No.: US 8,061,570 B1
(45) Date of Patent: Nov. 22, 2011

(54) QUICK RELEASE MASK BRACKET

(75) Inventors: Charles G. Holmes, Panama City, FL (US); Dennis G. Gallagher, Panama City, FL (US); William D. Olstad, Panama City, FL (US); William W. Hughes, III, Panama City, FL (US); Charles M. Edmondson, II, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/806,257

(22) Filed: Jul. 30, 2010

(51) Int. Cl.
*A42B 1/24* (2006.01)
(52) U.S. Cl. .................. 224/181; 222/422
(58) Field of Classification Search .......... 248/200, 248/205.1, 694; 2/425, 424, 41, 15, 422; 224/181, 271, 272, 930, 908, 909
See application file for complete search history.

(56) References Cited

U.S. PATENT DOCUMENTS

| | | | | |
|---|---|---|---|---|
| 4,920,585 A * | 5/1990 | Arai | | 2/424 |
| 2005/0015839 A1* | 1/2005 | Krzysik et al. | | 2/15 |
| 2009/0307828 A1* | 12/2009 | Ludlow | | 2/431 |
| 2010/0314401 A1* | 12/2010 | Chucales et al. | | 220/739 |
| 2011/0138520 A1* | 6/2011 | DeBoer | | 2/425 |

* cited by examiner

*Primary Examiner* — Ramon Ramirez
(74) *Attorney, Agent, or Firm* — James T. Shepherd

(57) ABSTRACT

An assembly for securing an apparatus to a facemask includes a U-shaped frame extending along similarly shaped portions of the facemask. Removable attachment clips secure the frame to the facemask. Two cylindrical pins with circumferential radiused grooves are attached to and extend from the top portion of the frame. The pins mate with bores in a clevis assembly, to which the apparatus can be attached. A spring-loaded bar spans between the bores. The bores in the clevis assembly receive the pins and the spring-bias causes the bar to engage with the grooves to secure the clevis assembly to the frame. A lever is rotatably attached to the clevis assembly. Pivoting the lever works against the spring-bias to lift the bar out of the grooves, disengaging the pins, and allowing the clevis assembly to be disengaged from the frame and facemask.

15 Claims, 3 Drawing Sheets

QUICK RELEASE MASK BRACKET

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates to an improvement for facemasks worn by divers, firefighters, or the like. More particularly, the present invention relates to an improvement for a bracket structure mountable on the outside of a facemask to secure an external apparatus to the facemask.

(2) Description of the Prior Art

Divers, firefighters, first responders and other workers that wear facemasks frequently need to be apprised of environmental and status information for the successful and safe completion of their work assignments. Such information can include details of their surroundings, environmental and ambient conditions, and data regarding depth, orientation, or status of their life-support breathing apparatus.

Typically, a diver is supplied with separate timers, pressure gauges and other displays for monitoring such critical information. In order to access the information, divers may need to rapidly attach or remove various accessories or apparatuses to their facemasks, including such devices as lights, cameras, head-mounted displays (HMDs), thermal imagers, night-vision devices and the like.

Some HMDs have been hard-mounted to a helmet or a full-facemask but these HMDs have not been usable with single strap Self Contained Underwater Breathing Apparatus (SCUBA) type facemasks. Some specialized masks have been manufactured with one type or another of display made as an integral part. However, such specialized masks can be costly and may not be suitable for other tasks or other work conditions.

Consequently, many different expensive masks would have to be kept in inventory for the different applications. As the technology for HMDs advances, so does their use. Thus, an inventory of expensive, specialized masks can become obsolete after a relatively short time.

In addition, new safety and job requirements are evolving that require divers to use HMDs while wearing certain mask types. The divers must still be able to quickly remove the HMD systems (e.g. for safety reasons), or to pass the systems to other divers. However, removal of a facemask underwater to make this removal or transfer is unacceptably hazardous, so that further development and improvements of this technology are needed.

Recent bracket designs for securing HMDs make it possible to mount a HMD to a facemask using strap assemblies in addition to the facemask straps. However, such designs are cumbersome and difficult to attach or remove underwater.

Thus, a need has been recognized in the state of the art for a means for securely positioning or indexing displays of information and other visual aids in the field of view of a wearer of a facemask that can be fitted onto and removed from the facemask to improve safety and operational effectiveness without unduly encumbering the facemask.

SUMMARY OF THE INVENTION

It is therefore a general purpose and primary object of the present invention to provide systems and methods for mounting an external apparatus to a facemask. An index bracket, assembly securely positions an external apparatus on a facemask.

The assembly includes a U-shaped frame having top and side portions. The frame extends along the similarly shaped top and side portions of the facemask. Removable attachment clips, tailored for the specific facemask, secure the frame to the facemask.

A quick release clevis mechanism interconnects the U-shaped frame and the external apparatus. The external apparatus connects to the clevis mechanism using a friction design in a manner known in the art to provide for flipping the accessory up and down, swiveling the accessory, or rotating the accessory with one hand.

Two cylindrical holding pins are spaced apart and affixed at the top portion of the frame. The pins extend orthogonally from the top portion of the frame away from the facemask and have a circumferential radiused groove at a distance from the facemask. The ends of the pins distant from the facemask have a frusto-conical shape.

The pins mate with bores in leg portions of the clevis mechanism. A spring-loaded bar spans between the leg portions, transverse to the axis of the bores. The ends of the bar are contained within slots parallel to the bar. The slots extend into the leg portions to intersect the bores, with the base of the slots being offset from the bore axis. The spring biases the bar against the base of the slot, such that the bar partially extends into the bore.

As the clevis mechanism is moved toward the frame, the pins extend into the bores and the ends of the pins displace the bar from the bore. Continuing to move the clevis mechanism toward the frame results in the pins further advancing into the bores until the spring-bias causes the bar to engage with the grooves on the pins so as to secure the clevis mechanism to the frame.

A lever is rotatably attached between the leg portions of the clevis mechanism. When pivoted about an axis parallel to the bar axis, the lever contacts the bar and works against the spring-bias to lift the bar out of the pin grooves. With the bar disengaged from the grooves, the clevis mechanism can be moved away from the frame to retract the pins from the bores and disengage the clevis mechanism from the frame.

In one embodiment, an index bracket assembly for positioning an external apparatus on a facemask having top and side rim portions includes a U-shaped frame having top and side portions consistent in shape with the top and side rim portions of the facemask. At least one clip is secured to the frame and removably compresses the top and/or side rim portions between the frame and the clip. Two or more holding pins are spaced apart and affixed to the frame. The pins extend orthogonally from the frame in a direction away from the facemask. A clevis mechanism has bores formed therein and each of the pins is accepted into one of the bores. The pins are releasably secured within the bores. The apparatus is secured to the clevis mechanism.

In one embodiment, a circumferential radiused groove is formed in each of the pins at a distance from the frame and the ends of the pins distant from the frame are frusto-conically shaped. A movable retaining bar is positioned transverse to and intersecting the bores in the clevis mechanism. The retaining bar is spring-biased to reside at least partially in the bores. As the ends of the pins are moved into the bores, the ends displace the retaining bar from the bores. As the pins advance further into the bores, the bar engages with the groove in each pin to secure the clevis mechanism to the frame. A lever is pivotally attached to the clevis mechanism, with a first end of the lever in contact with the bar. Pivoting the lever results in the first end of the lever disengaging the bar from the grooves.

In one embodiment, the clevis mechanism includes a base portion housing the bores and positioned adjacent the frame when the pins are secured within the bores. Appendages extend orthogonally from the base portion, with the bores extending through the base portion into the appendages. An apparatus bolt removably extends through the appendages and secures the apparatus between the appendages.

In one embodiment, a movable retaining bar spans transverse to and between the appendages. The ends of the bar extend into slots formed on opposed faces of the appendages. The slots and the ends of the bar intersect the bores in the appendages. At least one spring is positioned in each of the slots to bias the bar to reside at least partially in the bores. Movement of the frusto-conical ends of the pins into the bores displaces the retaining bar from the bores against the spring bias. The spring biases the bar to engage the grooves in the pins when the grooves are positioned in the slots. The engagement of the grooves by the bar secures the clevis mechanism to the frame.

In one embodiment, each clip includes a first leg orthogonal to the frame and positioned adjacent to the top or side rim portions of the facemask and having at least one threaded bore formed therein. The clip includes a second leg orthogonal to the first leg and extending a distance in a direction toward the facemask, so as to position the top or side rim portion between the frame and the second leg. A compression bolt extends through the frame and engages with each of the threaded bores. Threading the bolt into the bore compresses the top or side rim portion between the frame and the second leg.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DESCRIPTION OF THE INVENTION

Figure 1:
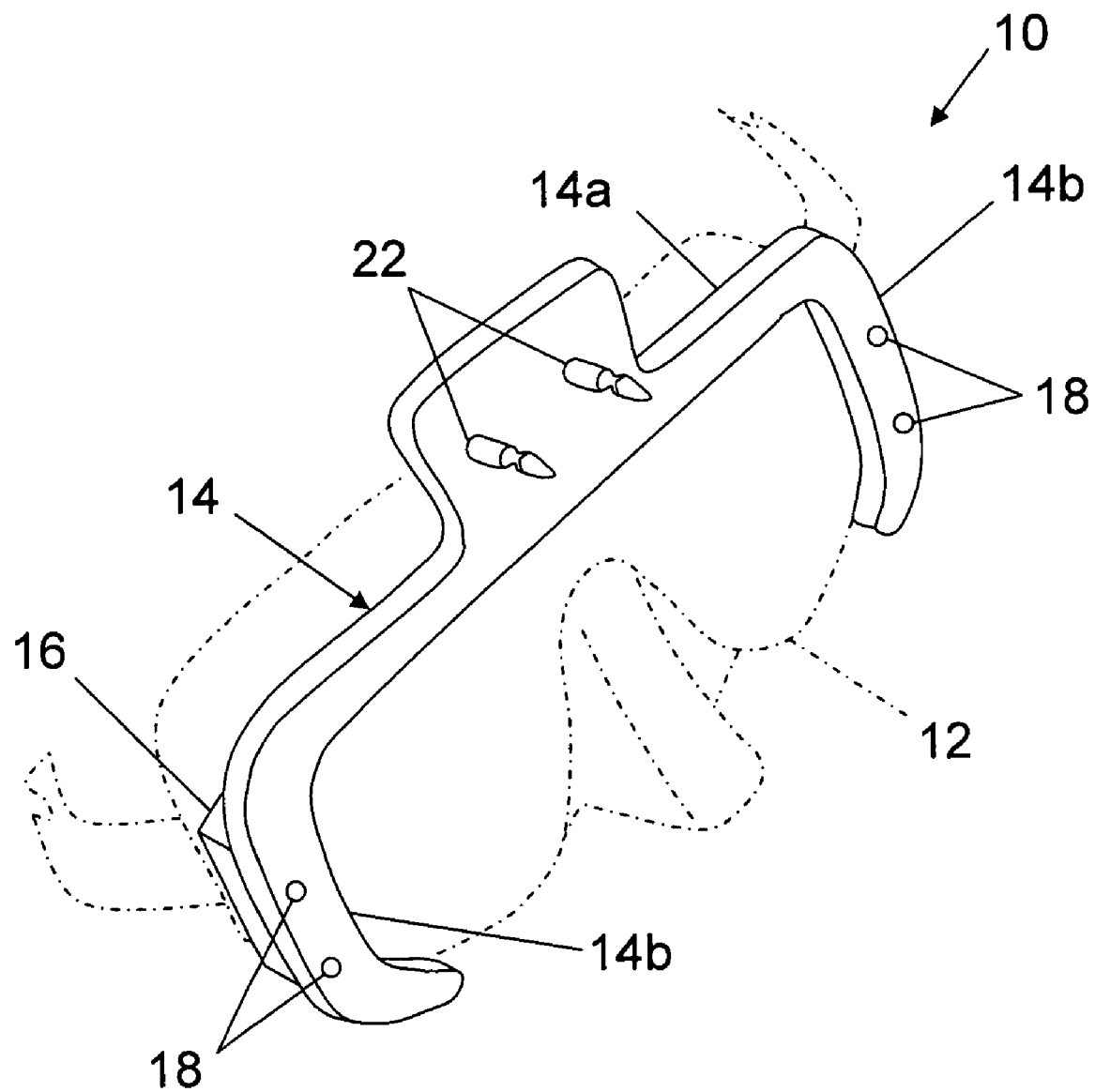
FIG. 1 illustrates a schematic side view of an index bracket assembly.

Referring now to FIG. 1, there is shown a schematic side view of index bracket assembly 10 attached to a representative SCUBA facemask 12 (shown in phantom). It will be understood by those of skill in the art that the exact configuration of index bracket assembly 10 will depend on the specific facemask to which assembly 10 will be attached. However, the features of assembly 10 described hereinafter apply equally to a multitude of facemask configurations.

U-shaped frame 14 of assembly 10 has a top portion 14a and side portions, 14b, that generally conform to the shape of facemask 12. Frame 14 is configured such that, when pressed against facemask 12, the obstruction of the diver's view through facemask 12 is minimized.

Figure 2:
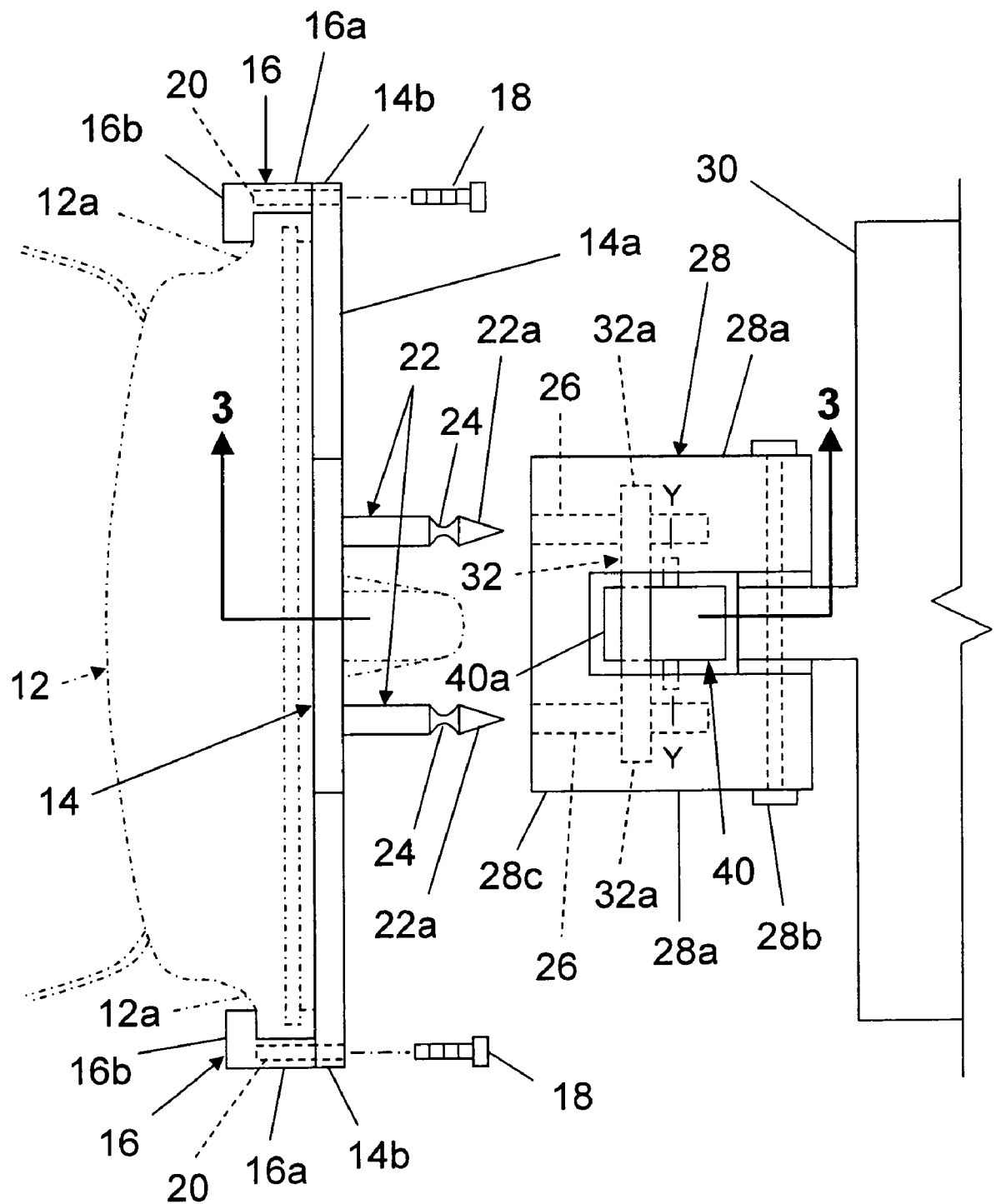
FIG. 2 illustrates a top view of an index bracket assembly and a clevis mechanism for securing an external apparatus to the bracket assembly.

Referring also to FIG. 2, there is shown a top view of the assembly 10 with frame 14 attached to mask 12. Clips 16 are removably attached to, and extend a distance along, leg portions 14b of frame 14 and secure frame 14 to facemask 12. For the exemplary embodiment illustrated in FIGS. 1 and 2, but not for limitation, clips 16 are L-shaped having first legs, 16a, orthogonal to frame 14 and second legs, 16b, distant from frame 14 and extending in a plane parallel to the plane of frame 14.

A width of leg portions 14b is such that leg portions 14b and first legs 16a of clips 16 extend beyond the perimeter of facemask 12. Bolts 18 extend through leg portions 14b and mate with threaded bores 20 in first legs 16a. As bolts 18 are tightened into threaded bores 20, second legs 16b are drawn towards frame 14 such that rim portions 12a of facemask 12 are compressed between second legs 16b and frame leg portions 14b. In this manner, frame 14 is held securely against facemask 12.

It will be understood by those of skill in the art that the exact configuration of clips 16 will depend on the specific facemask 12 to which frame 14 is attached. In addition, the foregoing description is not intended to limit the manner in which clips 16 secure frame 14 to facemask 12. Additional examples by which clips 16 secure frame 14 include clips 16 being spring loaded clips, draw bolt latch clips, cam latch clips, or other clip designs known in the art.

Two cylindrical holding pins 22 are spaced apart and affixed at top portion 14a of frame 14. Pins 22 extend orthogonally from top portion 14a in a direction away from facemask 12. Circumferential radiused grooves 24 are formed in pins 22 at a distance from facemask 12. Ends 22a of pins 22 distant from facemask 12 have a frusto-conical shape.

Pins 22 mate with bores 26 in clevis mechanism 28 (not shown in FIG. 1 for clarity). External accessory 30 is secured between clevis appendages 28a in a manner known in the art to provide for flipping accessory 30 up and down, swiveling accessory 30, or rotating accessory 30 with one hand.

Figure 3:
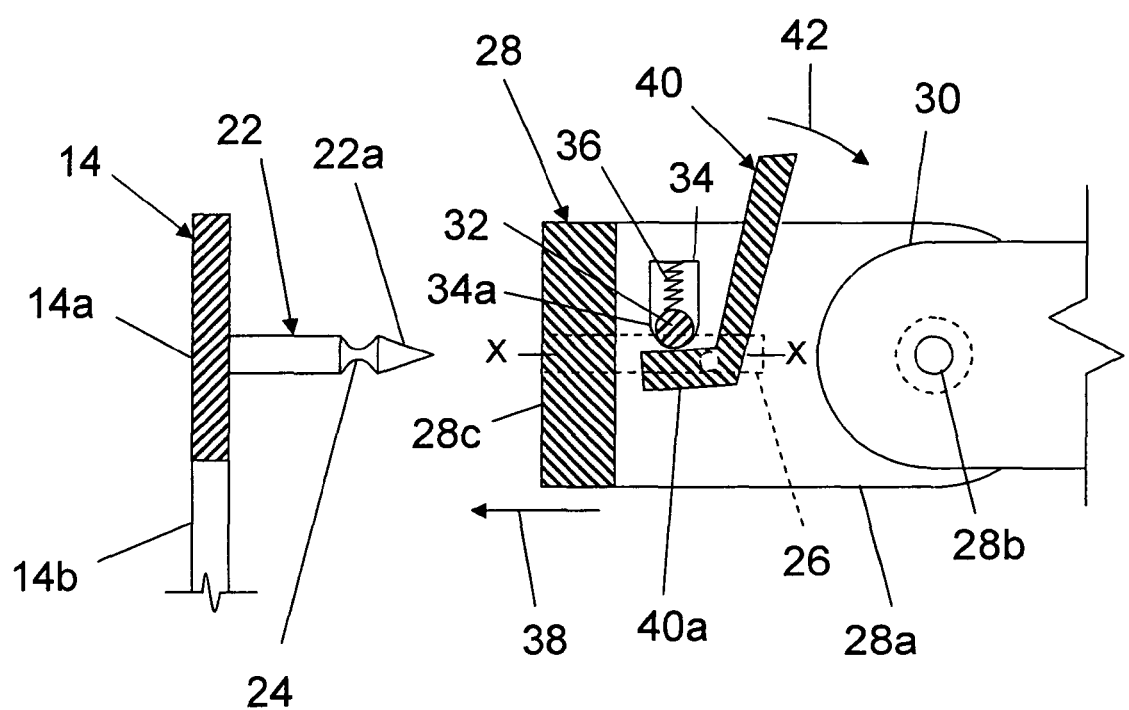
FIG. 3 is a cross-sectional view taken along line 3-3 of FIG. 2 showing the index bracket assembly and the clevis mechanism.

Referring also to FIG. 3; there is shown a cross-sectional view taken at line 3-3 of FIG. 2. For clarity, only a part of side portion 14b of frame 14 is shown and facemask 12 is not shown in FIG. 3. For the exemplary embodiment shown in FIGS. 2 and 3, bolt 28b secures accessory 30 between appendages 28a. Spring-loaded bar 32 spans between appendages 28a, transverse to axis X-X of bores 26. Ends 32a of bar 32 are contained within slots 34 formed in appendages 28a parallel to bar 32. Slots 34 extend into appendages 28a to intersect bores 26, with base 34a of slots 34 being offset from axis X-X of bores 26. Spring 36 biases bar 32 against base 34a of slot 34, such that bar 32 partially extends into bores 26.

As clevis mechanism 28 is moved toward frame 14 in the direction of arrow 38, pins 22 extend into bores 26 until frusto-conical ends 22a of pins 22 encounter bar 32. Further movement of clevis mechanism 28 toward frame 14 results in frusto-conical ends 22a displacing bar 32 from bores 26. Continuing to move clevis mechanism 28 toward frame 14 results in pins 22 further advancing into bores 26 until spring 36 biases bar 32 to engage with grooves 24 on pins 22 so as to secure clevis mechanism 28 to frame 14, with clevis base 28c being held against frame 14.

Lever 40 is rotatably attached between appendages 28a of clevis mechanism 28 so as to pivot about axis Y-Y, parallel to and offset from bar 32. When pivoted about axis Y-Y in a direction indicated by arrow 42, end 40a of lever 40 contacts bar 32 and works against the bias of spring 36 to lift bar 32 out of grooves 24 on pins 22. With bar 32 disengaged from grooves 24, clevis mechanism 28 can be moved away from frame 14 to retract pins 22 from bores 26 and disengage clevis mechanism 28 from frame 14.

What have thus been described are systems and methods for securing external apparatuses (camera, light, compass, head-mounted display, or the like) to a facemask while retaining the ability to remove the apparatuses quickly without dislodging or removing the mask. Index bracket assembly 10 provides a means to give facemask wearers an option for selectively viewing information (e.g., data provided by the external apparatuses) that can help in the performance of a task. Different external apparatuses 30 can be connected to index bracket assembly 10 for different tasks and the requirement for an inventory of different facemask structures is eliminated. Therefore, index bracket assembly 10, as disclosed herein is not to be construed as limiting, but rather, is intended to be demonstrative of this inventive concept.

Unlike prior art index brackets, the quick release feature embodied in pins 22, bores 26, bar 32 and lever 40, allows an operator to put on or remove an apparatus with one hand and without removing his/her mask. Each apparatus can be mounted on a clevis mechanism, ready for operation, without requiring the cumbersome underwater operation of unbolting the apparatus from the clevis mechanism.

Additionally, clips 16 provide for rigid attachment of the index bracket to the facemask. Clips 16 provide a significant improvement over securing the index frame with head straps, as in prior art index brackets. The head strap method can allow excessive movement of the apparatus relative to the dive mask, and in the case of critical alignment requirements, allows too much slop and movement for practical functionality.

Many modifications and variations of the present invention may become apparent in light of the above teachings. For example, with some facemask configurations, bar 32 may be readily accessible to the user. With such configurations, the user can directly move bar 32 against the bias of spring 36, without the need for lever 40 to lift bar 32 out of grooves 24. Further, as described hereinbefore, the configuration of clips 16 can be varied to suit the particular facemask to be used and the connection of clevis mechanism 28 to apparatus 30 can be varied to suit the particular apparatus to be used.

It will be understood that many additional changes in details, materials, steps, and arrangements of parts which have been described herein and illustrated in order to explain the nature of the invention, may be made by those skilled in the art within the principle and scope of the invention as expressed in the appended claims.

What is claimed is:

1. An index bracket assembly for positioning an external apparatus on a facemask having top and side rim portions, comprising:
   a U-shaped frame having top and side portions consistent in shape with the top and side rim portions of the facemask;
   at least one clip attached to said frame for removably compressing at least one of the top and side rim portions of the facemask between said frame and said at least one clip;
   at least two holding pins spaced apart and attached to said frame, said pins extending orthogonally from said frame in a direction away from the facemask;
   a clevis mechanism having bores formed therein, each of said pins being accepted into one of said bores and being releasably secured within said one bore, said apparatus being secured to said clevis mechanism; and
   means for attaching the external apparatus to said clevis mechanism.

2. The assembly of claim 1, wherein:
   each of said pins includes a circumferential radiused groove at a distance from said frame; and
   ends of said pins distant from said frame are frusto-conically shaped.

3. The assembly of claim 2, further comprising a movable retaining bar transverse to and intersecting said bores in said clevis mechanism, said retaining bar being spring-biased to reside at least partially in said bores, said ends of said pins displacing said retaining bar from said bores, said bar engaging said groove in each of said pins to secure said clevis mechanism to said frame.

4. The assembly of claim 3, further comprising a lever pivotally attached to said clevis mechanism, a first end of said lever in contact with said bar, wherein pivoting said lever disengages said bar from said grooves.

5. The assembly of claim 2, wherein said clevis mechanism further comprises:
   a base portion housing said bores, said base portion being positioned adjacent said frame when said pins are secured within said bores; and
   appendages extending orthogonally from said base portion, said bores extending through said base portion into said appendages.

6. The assembly of claim 5, further comprising a movable retaining bar transverse to and spanning between said appendages and intersecting said bores in said appendages, said retaining bar being spring-biased to reside at least partially in said bores, said ends of said pins displacing said retaining bar from said bores, said bar engaging said groove in each of said pins to secure said clevis mechanism to said frame.

7. The assembly of claim 6, further comprising a lever pivotally attached between said appendages, a first end of said lever in contact with said bar, wherein pivoting said lever about an axis parallel to said bar disengages said bar from said grooves.

8. The assembly of claim 7, wherein said means for attaching comprises an apparatus bolt removably extending through said appendages, said apparatus bolt securing the external apparatus between said appendages.

9. The assembly of claim 5, further comprising:
   a movable retaining bar transverse to and spanning between said appendages, ends of said bar extending into slots formed on opposed faces of said appendages and intersecting said bores in said appendages; and
   at least one spring positioned in each of said slots to bias said bar to reside at least partially in said bores, movement of said frusto-conical ends of said pins into said bores displacing said retaining bar from said bores against said spring bias, said spring biasing said bar to engage said grooves in said pins when said grooves are positioned adjacent to said slots, said engagement of said grooves by said bar securing said clevis mechanism to said frame.

10. The assembly of claim 9, further comprising a lever pivotally attached between said appendages, a first end of said lever in contact with said bar, wherein pivoting said lever about an axis parallel to said bar disengages said bar from said grooves.

11. The assembly of claim 10, wherein said at least one clip further comprises:
   a first leg orthogonal to said frame and positioned adjacent to at least one of the top and side rim portions of the facemask, said first leg having at least one threaded bore therein;

a second leg orthogonal to said first leg and extending a distance in a direction toward the facemask to position the at least one top and side rim portions of the facemask between said frame and said second leg; and at least one compression bolt extending through said frame and engaging said at least one threaded bore to compress the at least one top and side rim portions of the facemask between said frame and said second leg.

12. The assembly of claim 1, wherein said at least one clip further comprises:

a first leg orthogonal to said frame and positioned adjacent to at least one of the top and side rim portions of the facemask, said first leg having at least one threaded bore therein;

a second leg orthogonal to said first leg and extending a distance in a direction toward the facemask to position the at least one top and side rim portions of the facemask between said frame and said second leg; and at least one compression bolt extending through said frame and engaging said at least one threaded bore to compress the at least one top and side rim portions of the facemask between said frame and said second leg.

13. The assembly of claim 12, wherein:

each of said pins includes a circumferential radiused groove at a distance from said frame; and ends of said pins distant from said frame are frusto-conically shaped.

14. The assembly of claim 13, further comprising a movable retaining bar transverse to and intersecting said bores in said clevis mechanism, said retaining bar being spring-biased to reside at least partially in said bores, said ends of said pins displacing said retaining bar from said bores, said bar engaging said groove in each of said pins to secure said clevis mechanism to said frame.

15. The assembly of claim 14, further comprising a lever pivotally attached to said clevis mechanism, a first end of said lever in contact with said bar, wherein pivoting said lever disengages said bar from said grooves.

* * * * *